United States Patent [19]

Ames

[11] Patent Number: 5,021,665
[45] Date of Patent: Jun. 4, 1991

[54] OIL LEVEL MONITOR

[76] Inventor: Donald P. Ames, 914 Black Twig La., St. Louis, Mo. 63122

[21] Appl. No.: 457,093

[22] Filed: Dec. 26, 1989

[51] Int. Cl.$^5$ .............................................. G01F 23/28
[52] U.S. Cl. ................................ 250/357.1; 250/301; 250/461.1
[58] Field of Search ............... 250/301, 577, 357.1, 250/461.1; 73/293

[56] References Cited

U.S. PATENT DOCUMENTS

| | | | |
|---|---|---|---|
| 3,054,291 | 9/1962 | Landwer | 73/293 |
| 3,466,928 | 9/1969 | Kind | 73/293 |
| 4,155,013 | 5/1979 | Spiteri | 250/577 |
| 4,306,525 | 12/1981 | Faxvog | 123/196 |
| 4,440,022 | 4/1984 | Masom | 73/293 |
| 4,809,551 | 3/1989 | Grossiord | 73/327 |
| 4,897,551 | 1/1990 | Gersh et al. | 250/461.1 |

FOREIGN PATENT DOCUMENTS 55-70740  5/1980  Japan ................................ 250/301

OTHER PUBLICATIONS

Levy and Ames; "Monitoring Epoxy Cure Kinetics with a Viscosity Dependent Fluroescent Probe", Adhesive Chemistry 1984; pp. 245-256.
Levy and Ames; "Monitoring Epoxy Cure Kinetics with a Viscosity Dependent Fluorescence Probe"; Organic Coating and Applied Polymer Science Proceedings 48 Mar. 1983; pp. 116-120.
Levy and Ames; "Effect of Sorbed Water on Epoxy Fluorescence"; McDonnell Douglas Research Laboratories 85-21, Sep. 1985; pp. 1-5.
Levy and Schwab; "Monitoring the Composite Curing Process with a Fluorescence-Based Fiber-Optic Sensor"; Antec 1985; pp. 1530-1532.
Schwab and Levy; "Free-Volume-Dependent Fluorescence Probes of Physical Aging in Polymers"; Morl 88-221, pp. 1-14 and 535-545.
R. L. Levy; "A New Fiber-Optic Sensor for Monitoring the Composite-Curing Process"; Polymer Materials Science & Engineering 1986; pp. 321-324.
Schwab and Levy; "Advances in the Development of the Fluorescence Optrode Cure Sensor (FOCS)"; Polymer Materials Science & Engineering vol. 59, 1988; pp. 591-595.
Levy and Schwab; "Performance Characteristics of the Fluorescence Optrode Cure Sensor"; From Cross--Linked Polymers, Chapter 9, 1988; pp. 113-121.

*Primary Examiner*—Constantine Hannaher
*Attorney, Agent, or Firm*—Senniger, Powers, Leavitt & Roedel

[57] ABSTRACT

A fluid level monitor for sensing the level of fluid in a reservoir such as for sensing an oil level in an internal combustion engine crankcase containing a quantity of oil, the monitor includes a light source for generating a light beam having a frequency which causes fluorescence in the fluid and a fiber optic cable for transmitting the light beam to the reservoir for exciting the fluid in the reservoir to generate fluorescent radiation and for receiving the fluorescent radiation emitted by the fluid as a result of the excitation. The monitor also includes a photodetector for receiving the fluorescent radiation and for generating a signal which is a function of the intensity of the received fluorescent radiation and a display for receiving the signal to indicate the level of fluid in the reservoir.

24 Claims, 2 Drawing Sheets

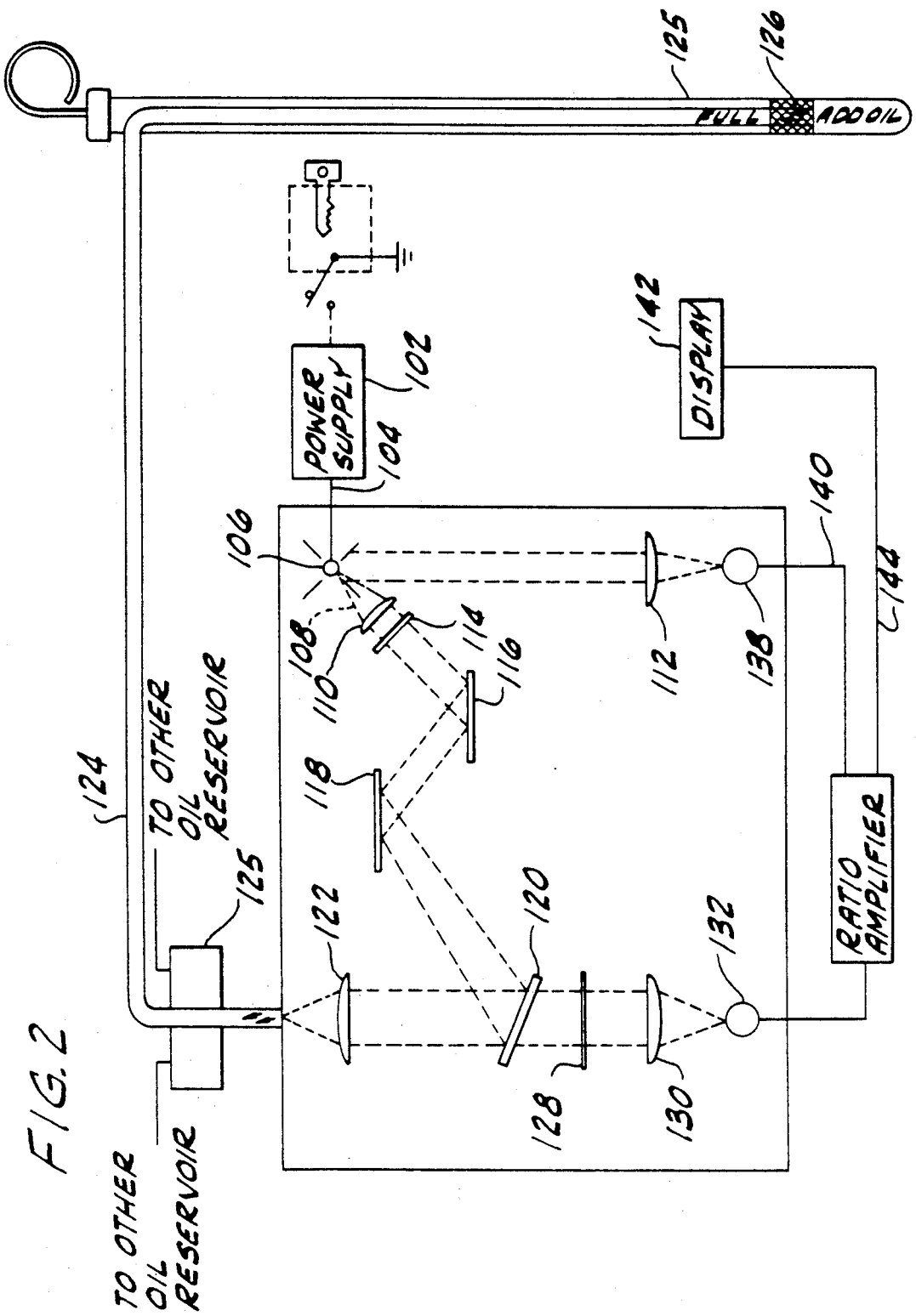

OIL LEVEL MONITOR

BACKGROUND OF THE INVENTION

This invention relates to an oil level monitor for any location where the oil level is critical for proper functioning such as a crankcase of an internal combustion engine. More particularly, the invention relates to an oil level monitor which determines the oil level by detecting through a fiber optic cable the intensity of fluorescent radiation emitted by engine oil when the oil is irradiated with the appropriate wavelengths of light.

It is desirable in an internal combustion engine to maintain the oil at a minimum level in the crankcase in order for the engine to function properly Typically, a dipstick having markings indicating the oil level is used to check the level of the oil in the crankcase. The dipstick is in contact with the oil and must be removed from the crankcase in order to check the oil level. Also, oil pressure switches are connected to the side of the crankcase to detect oil pressure in the engine. However, oil pressure switches only detect oil pressure and do not indicate when the oil level is below a minimum desired level. Additionally, detectors of many different constructions have been employed to monitor the oil level. However, these detectors typically require that the crankcase be modified to accept the detector.

SUMMARY OF THE INVENTION

Among the objects of the present invention are the provision of an oil level detector which can determine if oil in a crankcase is below a preselected level; the provision of an oil level detector which is convenient to use; and the provision of an oil level monitor which is reliable and economical.

Generally, a fluid level monitor for sensing the level of fluid in a reservoir such as for sensing an oil level in an internal combustion engine crankcase containing a quantity of oil comprises means for generating a light beam having a frequency which will cause fluorescence in the fluid, means for transmitting the light beam to the reservoir for exciting the fluid in the reservoir to generate fluorescent radiation, means for receiving the fluorescent radiation emitted by the fluid as a result of the excitation, means for generating a signal which is a function of the intensity of the received fluorescent radiation, and means for displaying the signal to indicate the level of the fluid in the reservoir.

In another form, the invention is an engine oil level monitor for an internal combustion engine having a crankcase containing a quantity of oil comprising means for generating radiation having a first wavelength, means for transmitting the first wavelength radiation to the crankcase to excite the oil in the crankcase to generate radiation having a second wavelength, means for receiving the second wavelength radiation, means for generating a first signal which is a function of the intensity of the first wavelength radiation, means for generating a second signal which is a function of the intensity of the second wavelength radiation, and means for comparing the first and second signals and for displaying the comparison to indicate the level of oil in the crankcase.

Other objects and features will be in part apparent and in part pointed out hereinafter.

BRIEF DESCRIPTION OF THE DRAWINGS

FIG. 2 is a schematic view of a second oil level monitor of the present invention.

Corresponding reference characters indicate corresponding parts throughout the several views of the drawings.

DETAILED DESCRIPTION OF THE PREFERRED EMBODIMENT

Figure 1:
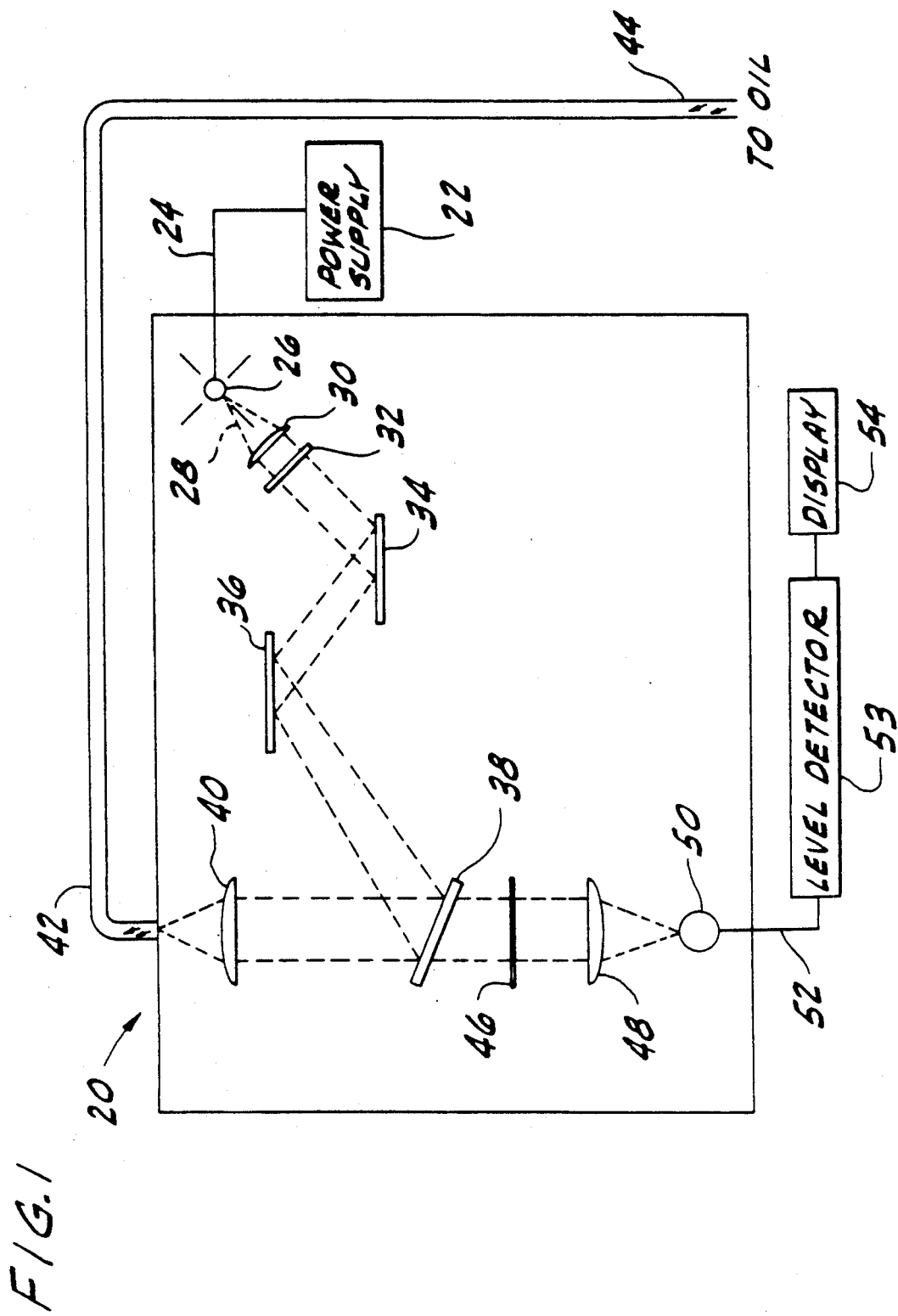
FIG. 1 is a schematic view of an oil level monitor of the present invention.

Referring now to FIG. 1, an oil level monitor of the present invention is indicated generally as 20 in the drawings. The monitor 20 includes a power supply 22 connected via line 24 supplying electrical power to illuminate a light source 26, such as a tungsten filament bulb or an injection laser. The light source 26 is a 100 milliwatt light source such as an injection laser producing radiation less than 340 nanometers (nm) in wavelength. For example, a gallium aluminum arsenide laser emitting at 900 nm. The laser frequency could be doubled twice or doubled and shifted to produce radiation with sufficient energy to induce fluorescence in the oil. A beam 28 produced by the light source 26 is expanded to a parallel light beam by a half convex (plano convex) lens 30. The beam 28 passes through an excitation filter 32 which absorbs all radiation having wavelengths above 340 nanometers (nm) and passes only light of wavelengths equal to or below about 340 mn. The beam 28 is reflected by dichroic mirrors 34, 36, and 38 to a half convex lens 40. Convex lens 40 focuses the beam 28 onto one end of a fiber optic cable 42. The cable 42 is 1-2 micrometers in diameter. The other end 44 of the fiber optic cable 42 is inserted through the oil dipstick opening (not shown) of a crankcase of an internal combustion engine, both of which are not shown. Alternatively, the invention may be used to sense the oil level of hydraulic brakes in automobiles and trucks, automatic transmissions, drive differentials and/or the wheel bearings on railroad cars.

The monitor 20 further includes an excitation filter 46 absorbing reflected radiation at or below 340 nm and another half convex lens 48 which focuses the fluorescent radiation on a photodetector 50. The photodetector 50 is connected via line 52 to a level detector 53 which includes an amplifier. Detector 53 provides a signal to a display 54 whenever photodetector 50 provides a signal above a preset level. Display 50, such as a backlit indicator light, signals the driver that the oil level in the reservoir is below a minimum desired level when the device is not operating. The display 54 is located on the instrument panel or dashboard of a car. For example, the monitor can indicate the oil level whenever the ignition switch is turned ON but neither the starter nor the engine are operating.

Preferably, the end 44 of the fiber optic cable 42 is supported, such as by a dip stick, to stabilize it when it is inserted in the oil reservoir. The end 44 of the fiber optic cable 42 is inserted through the dipstick opening of the crankcase and is positioned to contact the oil at the level at which the oil is to be monitored. For example, if the crankcase holds a maximum of 5 quarts of oil and it is desirable to know when the oil level is below 4.5 quarts, then the end 44 is positioned at the 4.5 quart level in the crankcase. The end 44 is coated with a polymer which is oil-phobic to present false readings from an adhering oil drop on the fiber end produced during engine operation. The cable 42 may be connected to the dipstick (see FIG. 2) at the desired level to be monitored.

In operation, the light beam 28 produced by the light source 26 is expanded by half convex lens 30 and the excitation filter 32 passes light having wavelengths at or below 340 nm. The beam 28 is reflected by the mirrors 34, 36, and 38. The beam 28 reflected by mirror 38 passes through half convex lens 40 which condenses the beam 28 onto the fiber optic cable 42. The fiber optic cable 42 transmits the light beam 28 to the engine oil in the crankcase through end 44 which contacts the oil. Molecular moeities present in additives in the oil are excited by the radiation in the light beam 28. When the radiation of the light beam 28 is absorbed by the oil additives the molecular moeities in the oil additives are excited from their normal ground state to higher energy states. The excited oil additive molecules return to the ground (equilibrium) state by releasing their excess energy as fluorescent electromagnetic radiation. The fluorescent radiation has wavelengths longer than the wavelength of the radiation of the light beam 28. The fluorescent radiation passes back through the fiber optic cable 42 without interfering with the radiation of the light beam 28. Radiation wavelengths are not attenuated appreciably while passing through fiber optic cable 42 as the attenuation is less than one decibel per 100 meters The fluorescent radiation is expanded by convex lens 40. The expanded radiation passes through the dichroic mirror 38 and filter 46 which absorbs the light beam 28 and passes the fluorescent radiation. The fluorescent radiation is focused by the half-convex condensing lens 48 onto photodetector 50. The signal provided over line 52 is amplified and displayed on the display 54.

A high level of fluorescence indicates that the end 44 of the cable 42 is in contact with the oil. A zero or low level of fluorescence signifies that the end 44 is not in contact with the oil and the oil level is below the desired level. The monitor 20 is operated preferably when the car is at rest. The monitor is operated upon acuation of the ignition switch.

If the oil additives in the crankcase do not contain molecular moeities which fluoresce, then a compound may be added to the oil to provide the required fluorescense signal. The compound is added in small amounts (less than 1% by volume).

In one preferred embodiment, it is contemplated that a fluorescent dye having a fluorescent yield which deteriorates over time and/or due to high temperatures may be added to the oil. As a result, the fluorescent radiation emitted would decrease with time so that, when the oil begins to degrade, very little fluorescent radiation would be emitted. A low level of fluorescence signifies that the oil has degraded and should be changed.

Referring now to FIG. 2, a second embodiment of the oil level monitor of the present invention is indicated generally as 100 in the drawings. The monitor 100 includes a power supply 102 connected via line 104 to a light source 106, such as a tungsten filament bulb or an injection laser. A beam 108 produced by the light source 106 is expanded to parallel light beams by convex lenses 110 and 113. The beam 108 passes through an excitation filter 114 which filters out light having a wavelength above 340 nm and passes only light of wavelengths equal to or below about 340 nm. The light beam 108 is reflected by dichroic mirrors 116, 118, and 120 to a half convex lens 122. Convex lens 122 focuses the beam 108 onto one end of one or more fiber optic cables 124 as selected by operator actuable switch 125. The other end 126 of the fiber optic cable 124 is inserted through the oil dipstick opening (not shown) of a crankcase of an internal combustion engine, both of which are not shown.

The monitor 100 further includes an excitation filter 128 and another convex lens 130. A photodetector 132 is connected via line 134 to a ratio amplifier 136. The ratio amplifier 136 is connected to a second photodetector 138 via line 140. Parallel light from source 106 as provided by lens 113 is focused on detector 138 by lens 112. The ratio amplifier 136 is also connected to a signal display 142 via line 144.

The end 126 of the fiber optic cable 124 is attached to dipstick 127 and inserted through the dipstick opening of the crankcase along with the dipstick 125. Cable 124 is positioned on the dipstick to contact the oil at the level at which the oil is to be monitored. For example, if the crankcase holds a maximum of 5 quarts of oil and it is desirable to know when the oil level is below 4.5 quarts, then the end 126 is positioned at the 4.5 quart level in the crankcase. The end 126 is coated with a polymer which is oil-phobic to repel any oil contacting the end 126 during engine operation.

In operation, part of the light beam 108 produced by the light source 106 is condensed by the convex lens 112 onto the photodetector 138. The other part of the light beam 108 is expanded by convex lens 110 and the excitation filter 114 passes light having wavelengths at or below 340 nm. The light beam 108 is reflected by the mirrors 116, 118, and 120. The beam 108 is reflected by mirror 120 through the convex lens 122 which condenses the beam 108 onto the fiber optic cable 124. The fiber optic cable 124 transmits the light beam 108 to the engine oil in the crankcase through end 124 which contacts the oil. Molecular moeities present in additives in the oil are excited by the radiation in the light beam 108. When the radiation of the light beam 108 is absorbed by the oil additives the molecular moeities in the oil additives are excited from their normal ground state to higher energy states. The excited oil additive molecules return to the ground (equilibrium) state by releasing their excess energy as fluorescent electromagnetic radiation. The fluorescent radiation has wavelengths longer than the wavelength of the radiation of the light beam 108. The fluorescent radiation passes back through the fiber optic cable 124 without interfering with the radiation of the light beam 108. Radiation wavelengths are not attenuated appreciably while passing through fiber optic cable 124 as the attenuation is less than one decibel per 100 meters. The fluorescent radiation is expanded by convex lens 122. The expanded radiation passes through the dichroic mirror 120 and filter 126 which absorbs the light beam 108 and passes the fluorescent radiation. The fluorescent radiation is focused by the condensing lens 130 onto photodetector 132. The signal provided over line 132 is compared to the signal provided over line 140. The result of this comparison is provided to the display 142 over line 144.

As is apparent to one skilled in the art, engine oil reservoirs cannot be monitored during engine operation because of the turbulence in the oil level caused by pumping. It is contemplated that this monitor according to the invention may be used in railroad cars to monitor differential oil levels thereby preventing hot box problems. In addition, the monitor may be used to sense the amount of a substance in a liquid. For example, most drugs have condensed aromatic compounds which fluoresce. The invention may be used to detect the concentration of drugs in the blood by contacting the end 44 of the optical fiber 42 with the blood being tested. In this case, the signal provided by photodetector 50 is compared to a reference and is proportional to the concentration of the drug in the blood.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. A fluid level monitor for sensing the level of fluid in a reservoir such as for sensing an oil level in an internal combustion engine crankcase containing a quantity of oil, the monitor comprising:
   means for generating a light beam having a frequency which will cause fluorescence in the fluid;
   means for transmitting the light beam to the reservoir for exciting the fluid in the reservoir to generate fluorescent radiation;
   means for receiving the fluorescent radiation emitted by the fluid as a result of the excitation;
   means for generating a signal which is a function of the intensity of the received fluorescent radiation;
   means, responsive to the intensity signal, for determining the level of fluid in the reservoir; and
   means for indicating the determined level of the fluid in the reservoir.

2. The monitor of claim 1 wherein the transmitting means comprises a fiber optic cable having one end at a preset level in the reservoir and the other end associated with the generating means and the receiving means.

3. The monitor of claim 2 wherein the end of cable in the reservoir has an oil-phobic coating thereon.

4. The monitor of claim 2 wherein the means for generating a light beam comprises a light source radiating light having a wavelength less than or equal to 340 nm.

5. The monitor of claim 2 wherein the generating means further comprises a light source and means for filtering out all wavelengths of light above 340 nm emitted by the light source and means for transmitting the filtered light to the fiber optic cable.

6. The monitor of claim 5 wherein the filtering means comprises an excitation filter and the transmitting means comprises diochroic mirrors and a plano convex lens for focusing the beam onto the fiber optic cable.

7. The monitor of claim 1 wherein the receiving means comprises means for filtering out substantially all wavelengths of the received fluorescent radiation below 340 nm and means for focusing the filtered fluorescent radiation on the signal generating means.

8. The monitor of claim 7 wherein the filtering means comprises an excitation filter and the focusing means comprises a plano convex lens.

9. The monitor of claim 1 wherein the signal generating means comprises a photodetector and amplifier for amplifying signals provided by the photodetector.

10. The monitor of claim 9 wherein the receiving means receives radiation transmitted back through the transmitting means.

11. A fluid level monitor for sensing contamination of a fluid in a reservoir such as for sensing contamination of oil in an internal combustion engine crankcase containing a quantity of oil, wherein the fluid includes an additive therein which emits fluorescent radiation when excited by the light beam wherein the amount of fluorescent radiation emitted by the additive decreases over time, the monitor comprising:
   means for generating a light beam having a frequency which will cause fluorescence in the fluid;
   means for transmitting the light beam to the reservoir for exciting the fluid in the reservoir to generate fluorescent radiation;
   means for receiving the fluorescent radiation emitted by the fluid as a result of the excitation;
   means for generating a signal which is a function of the intensity of the received fluorescent radiation;
   means for indicating when the signal falls below a preset level to indicate that the fluorescent properties of the additive have deteriorated.

12. The monitor of claim 11 wherein the indicating means indicates when the level of the fluid in the reservoir is below a predetermined minimum.

13. An engine oil level monitor for an internal combustion engine having a crankcase containing a quantity of oil, the monitor comprising:
   means for generating radiation having a first wavelength;
   means for transmitting the first wavelength radiation to the crankcase to excite the oil in the crankcase to generate radiation having a second wavelength;
   means for receiving the second wavelength radiation;
   means for generating a first signal which is a function of the intensity of the first wavelength radiation;
   means for generating a second signal which is a function of the intensity of the second wavelength radiation;
   means for comparing the first and second signals; and
   means for indicating the level of oil in the crankcase.

14. The monitor of claim 13 wherein the first wavelength is shorter than the second wavelength.

15. The monitor of claim 14 wherein the first wavelength is less than 340 nm and the second wavelength is equal to or greater than 340 nm.

16. The monitor of claim 14 wherein the comparing means comprises a ratio amplifier.

17. The monitor of claim 13 wherein the first radiation is a light beam and the second radiation is fluorescent radiation.

18. The monitor of claim 13 wherein the transmitting means comprises a fiber optic cable having one end at a preset level in the crankcase and the other end associated with the generating means and the receiving means.

19. The monitor of claim 18 further comprising a plurality of fiber optic cables, each associated with an oil reservoir and means for switching between the cables to associate one cable with the generating means.

20. The monitor of claim 13 wherein the receiving means receives radiation transmitted back through the transmitting means.

21. The monitor of claim 20 wherein the crankcase includes a dipstick and the end of the fiber optic cable in the crankcase is connected to the dipstick.

22. A fluid level monitor for sensing the level of fluid in a reservoir such as for sensing an oil level in an internal combustion engine crankcase containing a quantity of oil, the monitor comprising:
   a light source for generating a light beam having a frequency which causes fluorescence in the fluid;

a fiber optic cable for transmitting the light beam to the reservoir for exciting the fluid in the reservoir to generate fluorescent radiation and for receiving the fluorescent radiation emitted by the fluid as a result of the excitation, said cable having one end associated with the light source and the other end at a preset level in the reservoir;

a photodetector for receiving the fluorescent radiation and for generating a signal which is a function of the intensity of the received fluorescent radiation; and a display for indicating a low level of fluid in the reservoir when the signal indicates a level of fluid below a predetermined minimum level.

23. The monitor of claim 22 wherein the end of cable in the reservoir has an oil-phobic coating thereon.

24. The monitor of claim 22 wherein the light source has a wavelength of less than or equal to 340 nm and the photodetector detects radiation above said wavelength.

* * * * *